Figure 1:
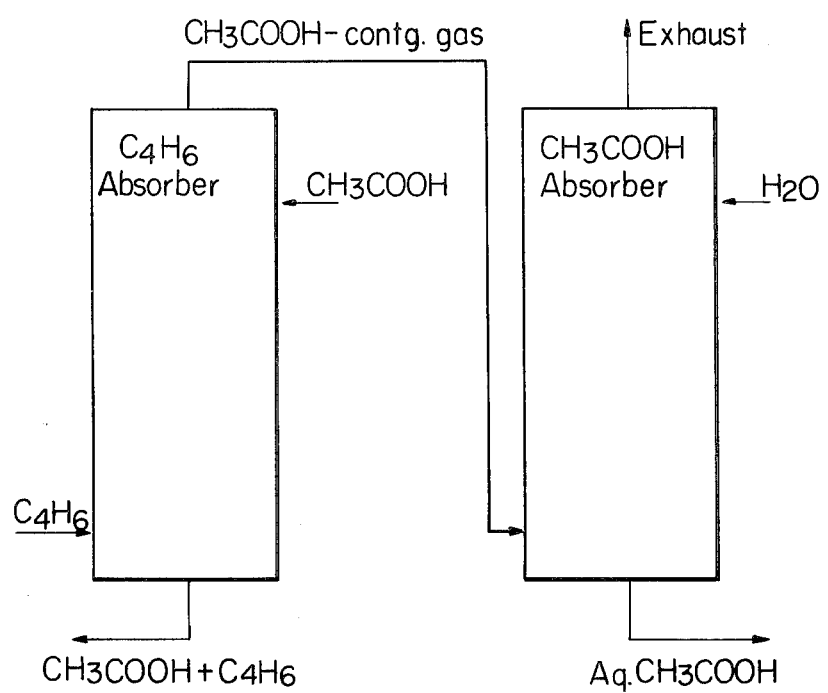

United States Patent [19]

Tanabe et al.

[11] 4,152,525

[45] May 1, 1979

[54] METHOD OF RECOVERING BUTADIENE GAS FROM AN ACETOXYLATION PROCESS

[75] Inventors: Yasuo Tanabe; Jun Toriya; Ikuo Kasahara, all of Kurashiki, Japan

[73] Assignee: Mitsubishi Chemical Industries Ltd., Tokyo, Japan

[21] Appl. No.: 545,504

[22] Filed: Jan. 30, 1975

[30] Foreign Application Priority Data

Feb. 5, 1974 [JP] Japan .................................. 49-14762

[51] Int. Cl.² ............................................ C07C 67/05
[52] U.S. Cl. ..................................... 560/244; 568/858
[58] Field of Search ........... 260/497 A, 497 R, 635 R; 560/244; 568/858

[56] References Cited

U.S. PATENT DOCUMENTS 3,872,163  3/1975  Schimizu ......................... 260/497 A

FOREIGN PATENT DOCUMENTS 1114475 10/1961 Fed. Rep. of Germany.
1170222 11/1969 United Kingdom.

OTHER PUBLICATIONS

Perry, "Perry's Chemical Engin. Handbook", 4th ed., pp. 14-1, 14-2 & 14-24 to 14-33 (1963).

*Primary Examiner*—James O. Thomas, Jr.
*Assistant Examiner*—Michael Shippen
*Attorney, Agent, or Firm*—Bierman & Bierman

[57] ABSTRACT

Disclosed is a method of recovering butadiene gas from an acetoxylation process which method comprises steps: (a) contacting a butadiene-containing gas with acetic acid to effect the absorption of butadiene in acetic acid, (b) recycling the acetic acid containing butadiene to the acetoxylation process, (c) contacting the waste gas containing acetic acid from step (a) with water to effect the absorption of acetic acid in water and (d) recycling the water containing acetic acid to hydrolysis step of the acetoxylation product.

14 Claims, 2 Drawing Figures

METHOD OF RECOVERING BUTADIENE GAS FROM AN ACETOXYLATION PROCESS

This invention relates to a method of recovering butadiene from the waste gas of an acetoxylation process comprising reacting butadiene, acetic acid and an oxygen-containing gas to produce acetoxybutene which is optionally further subjected to hydrolysis or hydrogenation and hydrolysis to produce butene diol or butane diol. In more particular, this invention provides an economical method in which butadiene in the waste gas from an acetoxylation step and purification system thereof is contacted with acetic acid thereby effecting absorption of butadiene in acetic acid and such acetic acid used is effectively recycled as a reactant for acetoxylation reaction.

It has already been known that butadiene, acetic acid and an oxygen-containing gas are reacted in the presence of a palladium catalyst to produce acetoxybutene; such acetoxybutene and acetoxybutane, which is a hydrogenation product, are subjected to hydrolysis then butene diol and butane diol are readily obtainable. Since the waste gas from acetoxylation step and purification system of acetoxylation product contains valuable components, such as butadiene and acetic acid, direct exhaustion of such waste gas results in not only an economic loss but air pollution.

Accordingly, this invention provides a closed system by which valuable components in such waste gas are effectively recovered thereby controlling air pollution. Thus, there are provided (1) a method of recovering butadiene from the waste gas of a process for producing diacetoxybutene by reacting butadiene, acetic acid and an oxygen-containing gas in the presence of a palladium catalyst, which comprises contacting butadiene-containing gas from acetoxylation system and purification system of the product with acetic acid in butadiene absorber to effect absorption of butadiene in acetic acid and recycling the acetic acid containing butadiene to the acetoxylation system, while contacting acetic acid-containing gas from the butadiene absorber with water in acetic acid absorber to remove acetic acid and (2) a method of recovering butadiene from the waste gas of a process producing butene diol and/or butane diol by reacting butadiene, acetic acid and an oxygen-containing gas in the presence of a palladium catalyst to produce diacetoxybutene which is hydrolyzed after optional hydrogenation, which comprises contacting butadiene-containing gas from acetoxylation system and purification system of the product with acetic acid in butadiene absorber to effect absorption of butadiene in acetic acid and recycling the acetic acid containing butadiene to the acetoxylation system, while contacting acetic acid-containing gas with water in acetic acid absorber to effect absorption of acetic acid in water and recycling water containing acetic acid to the hydrolysis step.

Examples of the waste gas containing butadiene and discharged from the acetoxylation system and purification system of the product and being subjected to the treatment according to this invention include, such as (1) a purge gas which is used for preventing the accumulation of an inert gas e.g. $N_2$ and $CO_2$ in the reaction system, (2) a flush gas which is obtained by decreasing the pressure of the reaction product solution obtained under super-pressure to ambient pressure to effect releasing the dissolved gas and (3) a gas which is released by removal of the dissolved gas from the reaction product prior to effecting distillation purification, for example a stabilizer gas.

Such waste gas usually contains oxygen, butadiene, acetic acid, carbon dioxide and in some case nitrogen and its composition varies depending upon the origin; however, it is essential to maintain the composition of outside the explosive range throughout the treatment.

The oxygen-containing gas which can be employed in this invention is, for example, oxygen, air and air diluted with an inert gas, such as carbon dioxide.

The acetic acid with which the waste gas is contacted to effect the absorption of butadiene is not critical and any acetic acid can be used including a commercially available product, a recovered acetic acid from, for example, the production of diacetoxybutene and the hydrolysis of diacetoxybutene and diacetoxybutane. However, caution should be taken so that the acetic acid does not contain the butadiene in an amount exceeding an equilibrium concentration of butadiene in acetic acid after treatment.

The process according to this invention will be explained referring to accompanied drawings which are flow sheets of the process. In FIG. 1, there are used a butadiene absorber and an acetic acid absorber. The waste gas containing butadiene is introduced into the butadiene absorber at lower portion and the acetic acid as absorbent is introduced at upper portion to effect a counter-current contact. It is desirable to maintain the temperature of such absorber as low as possible to obtain maximum absorption efficiency but it is required to be at a temperature above the freezing point of acetic acid (about 17° C.) and usually within a range of 20° to 80° C.

The lower limit of the pressure of the absorber depends upon the amount of butadiene to be absorbed and the amount of acetic acid which can be employed; of course, the higher the pressure the greater the absorption and, in general, a pressure of 0 to 150 kg/cm$^2$G, preferably 0 to 20 kg/cm$^2$G and in more particular 5 to 15 kg/cm$^2$G taking into consideration the economic factor.

It has been found that, in order to successfully perform the absorption of butadiene, the amounts of materials to be supplied into the absorber must satisfy the following relationship represented by the equation $$\frac{A + B}{I + B} \geq K$$

wherein A is mole of acetic acid, B is mole of butadiene, I is mole of other gases and K is gas-liquid equilibrium constant of butadiene-acetic acid. In practice, from the economic viewpoint, the relationship is usually within a range of $$100K \geq \frac{A + B}{I + B} \geq K$$

and preferably $$10K \geq \frac{A + B}{I + B} \geq 3K$$

The amount of acetic acid to be used varies depending upon the composition of the waste gas to be subjected to absorption treatment and it ranges usually from 1 to 10000 Kg per Kg of butadiene and preferably 10 to 1000 Kg. Any absorber which can be used for a conventional absorption process is conveniently employed, for example, a packed column, a plate column and a spray column.

The exhaust gas discharged from the top of the butadiene absorber contains only 50 ppm by volume or less of butadiene and is saturated with acetic acid. However, it may be possible to reduce the butadiene content by appropriately selection of the process conditions.

The exhaust gas containing acetic acid from the butadiene absorber is then introduced into the lower portion of an acetic acid absorber, while the acetic acid containing butadiene is discharged from the bottom of the absorber and supplied to an acetoxylation step.

At the upper portion, the acetic acid absorber is supplied with water which is free of acetic acid in an amount of 1 to 10000 Kg per Kg of acetic acid to be absorbed and preferably 10 to 1000 Kg. The conditions under which acetic acid absorption is carried out, such as temperature and pressure, are selected to similar to be those in the butadiene absorber.

If a large amount of water is employed in the acetic acid absorption, then the absorption efficiency increases but decreases the concentration of acetic acid in water after treatment. Of course, it is sufficient to use the minimum amount of water, especially it is desirable to use as little water as is required to effect hydrolysis of diacetoxybutane and diacetoxybutene where the water containing acetic acid is reused for such hydrolysis.

The exhaust gas from the top of the acetic acid absorber contains only 50 ppm by volume or less of acetic acid and this is evidence of the effectiveness of the process according to this invention.

Figure 2:
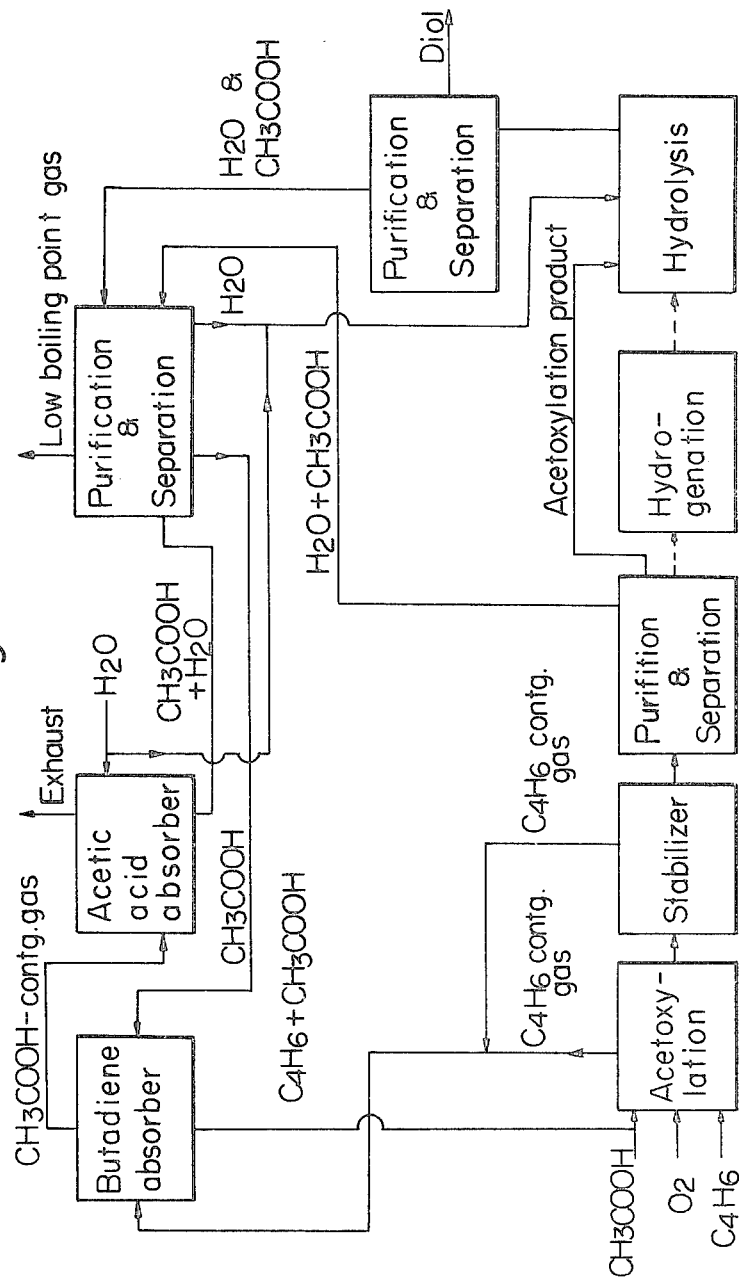

Referring to FIG. 2, another embodiment of the process according to this invention and involving acetoxylation and hydrolysis of diacetoxybutene or diacetoxybutane will be explained.

Acetoxylation and treatment of the product

Acetic acid, an oxygen-containing gas and butadiene are supplied to an acetoxylation system in which an acetoxylation catalyst composed of palladium compound and cocatalyst, such as a Redox system of palladium salt and copper salt and a supported catalyst of metallic palladium and a cocatalyst selected from the group consisting of Bi, Se, Sb and Tl on a supporter such as active carbon, silica and alumina is packed. The acetoxylation is usually carried out at a temperature of 40° to 180° C., preferably 60° to 150° C., and usually under a pressure above normal pressure, preferably 5 to 200 atm. The acetoxylation product is optionally subjected to degasification in a stabilizer to separate a butadiene-containing gas.

The degassed acetoxylation product is purified, for example by distillation to remove water, acetic acid and low boiling point byproducts and then subjected to hydrolysis treatment in a reactor packed with an acidic catalyst such as a hydrolysis catalyst of sulfonic acid type cation exchange resin at a temperature of 50° to 100° C. The hydrolysis product is subjected to distillation to separate acetic acid and water which are supplied to a subsequent purification and separation step, while the remaining fraction containing butene diol is purified to obtain the desired product of butene diol. Acetic acid separated from the purification and separation step is supplied to the butadiene absorber.

Where the production of butane diol is desired, the purified acetoxybutene is hydrogenated with hydrogen in the presence of a conventional hydrogenation catalyst, such as supported palladium and nickel catalysts at a temperature of room temperature to 200° C., preferably 50° to 150° C. to obtain acetoxybutane.

The acetoxybutane so produced is subjected to hydrolysis using procedures similar to those used for acetoxybutene.

Gas supply to butadiene absorber

The butadiene-containing gases to be supplied to the butadiene absorber are all or part of the waste gas from the acetoxylation and the released gas from the gas stabilizer and they may be supplied separately or in combination.

Cycle of acetic acid

Acetic acid discharged from the purification and separation system and from hydrolysis step, if it is employed, is separately supplied to a butadiene absorber in which counter contact of acetic acid and butadiene-containing gas is effected. The acetic acid containing butadiene from the absorber is recycled to the acetoxylation system as part of the acetoxylation raw material.

On the other hand, acetic acid-containing gas from the butadiene absorber is supplied to an acetic acid absorber to which fresh water is also supplied to ensure a counter contact to effect absorption of acetic acid in water. Water containing acetic acid discharged from the acetic acid absorber is supplied to the hydrolysis step after subjecting it to purification, if desired, to remove low boiling point contaminants.

The exhaust gas from which acetic acid has been removed no longer contains any valuable components many of which are toxic.

According to this invention, there is provided a closed system in which butadiene in the waste gas is recovered by absorption in acetic acid and is recycled to the acetoxylation step, and further the acetic acid used for such butadiene recovery is also collected by simply washing with water which may be then used for hydrolysis of the acetoxylation product, whereby environmental pollution is avoided.

If such washed water is not used for the hydrolysis, the water containing acetic acid is subjected to a biochemical treatment to make it nontoxic.

This invention will be explained in detail referring to the following Examples without intention to limit this invention.

EXAMPLE 1

Through a packed layer of a catalyst of palladium-selenium supported on active carbon was continuously passed acetic acid (400 Kg/hr), butadiene (120 Kg/hr) and 6% oxygen-containing gas (734 Nm$^3$/hr) to effect acetoxylation reaction to obtain a waste gas having the following composition:

| Component | Proportion (vol %) |
| --- | --- |
| butadiene | 0.66 |
| oxygen | 2.84 |
| nitrogen | 94.89 |
| carbon dioxide | 1.58 |
| acetic acid | 0.03 |

In FIG. 1, the butadiene absorber used was 500 mm in internal diameter and had a packed layer of 300 mm in height (packed with 25 mm of Raschig rings) and an acetic acid absorber was 300 mm in internal diameter and had a packed layer of 2000 mm in height (packed with 25 mm of Raschig rings) and both were operated at a temperature of 40° C. under a pressure of 5 Kg/cm$^2$G.

The butadiene absorber was charged with the waste gas having the above composition at a rate of 720 Nm$^3$/hr and acetic acid at a rate of 3180 Kg/hr, and to the acetic acid absorber was charged with demineraled water at a rate of 104 Kg/hr. The respective content of butadiene and acetic acid in the exhaust gas from the acetic acid absorber was less than 50 ppm, said concentration being less than the lowest detectable limit.

The acetic acid from the butadiene absorber contained 0.35 wt% of butadiene and a minute amount of carbon dioxide and nitrogen. All of the acetic acid was supplied to the acetoxylation system as part of the acetic acid raw material.

From the acetic acid absorber, water containing 1.0 wt% of acetic acid was obtained and it was used as part of the water to be supplied to hydrolysis reaction of diacetoxybutene, however, no trouble was observed during the hydrolysis.

EXAMPLE 2

In this Example, the process was carried out according to the procedures illustrated in FIG. 2 and the operation conditions and the absorbers employed were similar to those in Example 1 except that the pressure of the absorbers was 10 Kg/cm$^2$G, respectively.

In a steady state, the materials supplied to the packed layer of catalyst of palladium-selenium supported on active carbon were acetic acid (67 Kg mole/hr), butadiene (2.0 Kg mole/hr) and 7.2% oxygen-containing nitrogen (33.2 Kg mole/hr) at a temperature 80° to 100° C. under a pressure of 30 Kg/cm$^2$G to effect the acetoxylation. A waste gas having the following composition was obtained and was supplied to the butadiene absorber.

| Component | Proportion (Kg mole/hr) |
| --- | --- |
| oxygen | 0.7 |
| nitrogen | 30.8 |
| carbon dioxide | 0.5 |
| butadiene | 0.2 |
| Total | 32.2 |

On the other hand, the acetoxylation product was subjected to distillation treatment to obtain acetic acid (62.8 Kg mole/hr) and water (2.5 Kg mole/hr) which were supplied to a purification and separation tower. To a hydrolyzing apparatus which was packed with a sulfonic acid type cation exchange resin (available from Mitsubishi Chemical Industries Ltd. Tokyo, Japan, under name of SKIB) were supplied diacetoxybutene from the acetoxylation step and water containing 4.2 mole% of acetic acid at a rate of 19.8 Kg mole/hr from the purification and separation tower to effect hydrolysis at a temperature of 60° to 90° C. The hydrolysis product was subjected to distillation to remove acetic acid (4.6 Kg mole/hr) and water (15.2 Kg mole/hr) which were introduced into the purification and separation tower.

The acetic acid recovered in the purification and separation tower was supplied to the butadiene absorber at a rate of 66.7 kg mole/hr.

The exhaust gas containing 0.3 mole% of acetic acid from the top of the butadiene absorber was supplied at a rate of 32.1 Kg mole/hr to the acetic acid absorber to which water was also supplied at a rate of 1.7 Kg mole/hr. The exhaust gas from the top of the acetic acid absorber contained less than 50 ppm by volume, respectively, butadiene and acetic acid.

Water containing 6.6 mole% of acetic acid was removed from the bottom of the acetic acid absorber at a rate of 1.6 Kg mole/hr and was then supplied to the purification and separation apparatus.

Acetic acid containing 0.3 mole% of butadiene was separated from the bottom of the butadiene absorber at a rate of 67.0 Kg mole/hr and was recycled to the acetoxylation system. Fresh acetic acid was added to the recycled acetic acid to replace the acetic acid consumed during the process.

After subjecting the hydrolysis product to purification, crude butene diol was obtained at a rate of 1.9 Kg mole/hr.

EXAMPLE 3

The acetoxylation reaction was followed by the procedures similar to those used in Example 1, but the oxygen-containing gas was air diluted with carbon dioxide to obtain a waste gas of the following composition at a rate of 730 Nm$^3$/hr.

| Component | Proportion (vol %) |
| --- | --- |
| butadiene | 0.67 |
| oxygen | 2.89 |
| nitrogen | 23.19 |
| carbon dioxide | 73.21 |
| acetic acid | 0.04 |

The waste gas was treated according to the procedures in Example 1 and the exhaust comprised $O_2$, $N_2$, $CO_2$ and $H_2O$ as well as 70 ppm by volume of butadiene and less than 50 ppm by volume of acetic acid.

The composition of the acetic acid containing butadiene from the butadiene absorber was similar to that of Example 1 and all of said acetic acid was supplied to the acetoxylation system as part of the acetic acid raw material.

EXAMPLE 4

Referring to FIG. 1, the butadiene absorber was 200 mm in internal diameter and had a packed layer of 3000 mm in height (packed with 15 mm of Raschig rings) and the acetic acid absorber was 120 mm in internal diameter and had a packed layer of 2000 mm in height (packed with 10 mm of Raschig rings), and both absorbers were maintained at a temperature of 40° C. under normal pressure. The butadiene absorber was supplied with a waste gas of the following composition at a rate of 18.8 Nm$^3$/hr and acetic acid at 600 Kg/hr, while the acetic acid absorber was supplied with demineraled water at 18 Kg/hr.

| Component | Proportion (Kg mole/hr) |
| --- | --- |
| butadiene | 0.42 |
| oxygen | 0.04 |
| nitrogen | 0.03 |
| carbon dioxide | 0.35 |
| acetic acid | 0.00 |

The resultant exhaust gas contained 115 ppm by volume of butadiene and less than 50 ppm by volume of acetic acid.

EXAMPLE 5

In this Example, the absorbers and the operation conditions employed were similar to those in Example 4 and the treatment of a waste gas was carried out using the closed system illustrated in FIG. 2.

In a steady state, through a packed layer of a catalyst of palladium-selenium supported on active carbon were passed acetic acid (550 Kg mole/hr), butadiene (18 Kg mole/hr) and 83.8% oxygen-containing gas (13.6 Kg mole/hr) at a temperature of 60° to 80° C. under a pressure of 5 Kg/cm²G to effect acetoxylation. A waste gas having the following composition from the reactor was supplied to a butadiene absorber at a rate of 8.2 Kg mole/hr.

| Component | Proportion (Kg mole/hr) |
| --- | --- |
| oxygen | 0.4 |
| nitrogen | 0.3 |
| carbon dioxide | 3.5 |
| butadiene | 4.2 |

The acetoxylation product was subjected to distillation to separate acetic acid (514.8 Kg mole/hr) and water (41.7 Kg mole/hr) which were further purified. The remaining diacetoxybutene was supplied to a hydrolysis step to which also supplied was water containing about 4 mole% of acetic acid (91.7 Kg mole/hr) discharged from the purification system. The hydrolyzed product was subjected to a distillation to remove acetic acid (38.9 Kg mole/hr) and water (52.8 Kg/hr) which were supplied to a purification and separation tower from which 96 mole% acetic acid was recovered at a rate of 57.3 Kg mole/hr and was recycled to the butadiene absorber.

The waste gas (4.4 Kg mole/hr) from the butadiene absorber contained 4.5 mole% of acetic acid and was supplied to the acetic acid absorber to which water (16.7 Kg mole/hr) was also supplied. The exhaust gas from the absorber contained 115 ppm by volume of butadiene and less than 50 ppm of acetic acid. The water discharged from the acetic acid absorber and containing 1.2 mole% of acetic acid was supplied to a purification and separation tower at a rate of 16.6 Kg mole/hr, on the other hand, the acetic acid discharged therefrom contained 0.7 mole% of butadiene and was recycled to the acetoxylation system together with fresh acetic acid in an amount corresponding to that lost during the operation.

The desired product of crude butene diol was obtained from the hydrolysis step at a rate of 17.6 Kg mole/hr.

What is claimed is:

1. In a method for producing diacetoxybutene and a waste gas containing butadiene by acetoxylation of butadiene, acetic acid and an oxygen containing gas in a reaction zone in the presence of a palladium catalyst and an absorption medium for butadiene, the improvement comprising contacting at least a part of said waste gas with an absorption medium consisting essentially of acetic acid in an amount between about 1 and 10,000 parts by weight per part of butadiene in said waste gas at a temperature of 20° to 80° C. and a pressure from 0 to 150 Kg/cm²G. to form a mixture containing acetic acid and butadiene and a gaseous effluent containing acetic acid, recycling said mixture to said reaction zone, and contacting at least part of said gaseous effluent with water in an amount between 1 and 10,000 parts by weight per part of acetic acid in said effluent at a temperature of from 20° to 80° C. and a pressure of from 0 to 150 Kg/cm²G. to remove acetic acid therefrom.

2. The method according to claim 1 wherein said diacetoxybutene is purified after said reaction, thereby producing additional butadiene-containing waste gas, wherein the improvement further comprises contacting at least part of said additional waste gas with said absorption medium.

3. The method according to claim 1 wherein said butadiene is absorbed at a temperature of from 20 to 80° C. and a pressure of from 0 to 20 kg/cm²G.

4. The method according to claim 1 wherein said acetic acid in said medium is present in an amount of from 10 to 1,000 parts by weight per part of said butadiene.

5. The method according to claim 1 wherein said effluent is absorbed at a temperature of from 20 to 80° C. and a pressure of from 0 to 20 kg/cm²G.

6. The method according to claim 5 wherein said effluent is absorbed at a pressure of from 5 to 15 kg/cm²G.

7. The method according to claim 1 wherein said water is present in an amount of from 10 to 1,000 parts by weight per part of said acetic acid in said effluent.

8. In a method for producing butenediol by the hydrolyzation of diacetoxy butene formed from the acetoxylation of butadiene, acetic acid, and an oxygen containing gas in a reaction zone in the presence of a palladium catalyst and an absorption medium for butadiene to thereby form diacetoxybutene and a waste gas containing butadiene, the improvement comprising contacting at least part of said waste gas with an absorption medium consisting essentially of acetic acid in an amount between about 1 and 10,000 parts by weight per part of butadiene in said waste gas at a temperature of from 20° to 80° C. and a pressure of 0 to 150 kg/cm²G. to form a mixture containing acetic acid and butadiene and a gaseous effluent containing acetic acid, recycling said mixture to said reaction zone, and contacting at least part of said gaseous effluent with water in an amount between about 1 and 10,000 parts by weight per part of acetic acid in said effluent at a temperature of from 20 to 80° C. and a pressure of from 0 to 150 Kg/cm²G. to form aqueous acetic acid, and returning said aqueous acetic acid to the hydrolyzation step.

9. The method according to claim 8 wherein said diacetoxybutene is purified after said reaction, thereby producing additional butadiene-containing waste gas, wherein the improvement further comprises contacting at least part of said additional waste gas with said absorption medium.

10. In a method for producing butanediol by the hydrolyzation of diacetoxybutane which is formed by the hydrogenation of diacetoxybutene, said diacetoxybutene formed from the acetoxylation of butadiene, acetic acid and an oxygen containing gas in a reaction zone in the presence of a palladium catalyst and an absorption medium for butadiene to thereby form diacetoxybutene and a waste gas containing butadiene, the improvement comprising contacting at least a part of said waste gas with an absorption medium consisting essentially of acetic acid in an amount between about 1 and 10,000 parts by weight per part of butadiene in said waste gas at a temperature of from 20° to 80° C. and a pressure of from 0 to 150 kg/cm²G. to form a mixture containing acetic acid and butadiene and a gaseous effluent containing acetic acid, recycling said mixture to said reaction zone, and contacting at least part of said gaseous effluent with water in an amount between about 1 and 10,000 parts by weight per part of acetic acid in said effluent at a temperature of from 20° to 80° C. and a pressure of from 0 to 150 kg/cm²G. to form aqueous acetic acid, and returning said aqueous acetic acid to the hydrolyzation step.

11. A method according to claim 10 wherein said diacetoxybutane is purified after said reaction, thereby producing additional butadiene-containing waste gas, wherein the improvement further comprises contacting at least part of said additional waste gas with said absorption medium.

12. The method according to claim 10 wherein said butadiene is absorbed at a pressure of from 5 to 15 kg/cm²G.

13. A process for producing butenediol which comprises:
   (a) reacting butadiene, acetic acid and an oxygen-containing gas in the presence of a palladium catalyst in a reaction zone at a temperature of 40° to 180° C. in a liquid phase to form waste gas and an acetoxylation product diacetoxybutene,
   (b) subjecting said product to distillation after effecting degasification thereof to remove gases including butadiene,
   (c) introducing to a butadiene absorption zone the butadiene-containing gas from step (b) and at least a part of said waste gas,
   (d) supplying acetic acid in an amount of 1 to 10,000 parts by weight per part of butadiene in the gas of step (c) to said butadiene absorption zone while maintaining a temperature of 20 to 80° C. and a pressure of 0 to 20 Kg/cm²G,
   (e) recycling the acetic acid-containing butadiene from the butadiene absorption zone to said reaction zone,
   (f) supplying acetic acid containing gaseous effluent from said butadiene absorption zone to an acetic scrubbing zone, said scrubbing zone being at a temperature of 20 to 80° C. and a pressure of 0 to 20 Kg/cm²G,
   (g) contacting said gaseous effluent with water in said scrubbing zone in an amount required for hydrolysis of said acetoxylation product obtained from step (b),
   (h) charging the water containing acetic acid removed from said scrubbing zone into a hydrolysis zone, and
   (i) hydrolysing said acetoxylation product in the presence of an acid type cationic exchange resin at a temperature of 50 to 100° C.

14. A process for producing butanediol which comprises:
   (a) reacting butadiene, acetic acid and an oxygen-containing gas in the presence of a palladium catalyst in a reaction zone at a temperature of 40° to 180° C. in a liquid phase to form waste gas and an acetoxylation product diacetoxybutene,
   (b) subjecting said product to distillation after effecting degasification thereof to remove gases including butadiene,
   (c) hydrogenating the diacetoxylation product from step (b) in the presence of a hydrogenation catalyst at a temperature of 50 to 150° C. to obtain diacetoxybutane which is introduced into a hydrolysis reactor,
   (d) introducing to a butadiene absorption zone the butadiene-containing gas from step (b) and at least a part of said waste gas,
   (e) supplying acetic acid in an amount of 1 to 10,000 parts by weight per part of butadiene in the gas of step (c) to said butadiene absorption zone while maintaining a temperature of 20 to 80° C. and a pressure of 0 to 20 kg/cm²G,
   (f) recycling the acetic acid containing butadiene from the butadiene absorption zone to said reaction zone,
   (g) supplying acetic acid containing gaseous effluent from said butadiene absorption zone to an acetic acid scrubbing zone, said scrubbing zone being at a temperature of 20 to 80° C. and a pressure of 0 to 20 Kg/cm²G,
   (h) contacting said gaseous effluent with water in said scrubbing zone in an amount required for hydrolysis of said acetoxylation product obtained from step (b),
   (i) charging the water containing acetic acid removed from said scrubbing zone into a hydrolysis zone, and
   (j) hydrolyzing said hydrogenation product diacetoxybutane in the presence of an acid type cationic exchange resin at a temperature of 50 to 100° C.

* * * * *